United States Patent [19]

Vilkomerson et al.

[11] 4,249,539

[45] Feb. 10, 1981

[54] ULTRASOUND NEEDLE TIP LOCALIZATION SYSTEM

[75] Inventors: David H. R. Vilkomerson, Princeton; Reuben S. Mezrich, Rocky Hill; Carl S. Rubin, Cherry Hill, all of N.J.

[73] Assignee: Technicare Corporation, Solon, Ohio

[21] Appl. No.: 10,564

[22] Filed: Feb. 9, 1979

[51] Int. Cl.³ ............................................. A61B 10/00
[52] U.S. Cl. ..................................... 128/660; 128/754
[58] Field of Search ............ 128/660, 661, 754, 24 A

[56] References Cited

U.S. PATENT DOCUMENTS

| | | | |
|---|---|---|---|
| 3,556,079 | 1/1971 | Omizo | 128/661 |
| 3,721,227 | 3/1973 | Larson et al. | 128/660 |
| 4,029,084 | 6/1977 | Soldner | 128/660 |
| 4,058,114 | 11/1977 | Soldner | 128/754 X |
| 4,108,165 | 8/1978 | Kopp et al. | 128/660 |

FOREIGN PATENT DOCUMENTS 2455401  5/1975  Fed. Rep. of Germany ........... 128/660

OTHER PUBLICATIONS

*Time*, Oct. 2, 1964, p. 96.

*Primary Examiner*—Kyle L. Howell
*Attorney, Agent, or Firm*—Audley A. Ciamporcero, Jr.

[57] ABSTRACT

A B-scan pulse echo ultrasound system produces a real time image of a body area under inquiry, and an aspiration needle is inserted directly into that area. The needle carries a small, omni-directional ultrasound transducer, electrically connected through the needle to transponder electronics. Incident pulses from the imaging transducer to the omni-directional transducer are sensed at the latter, and the position thereof is inserted into the image either by generation of a return signal from the needle point, or through delay logic and subsequent production of a composite.

10 Claims, 4 Drawing Figures

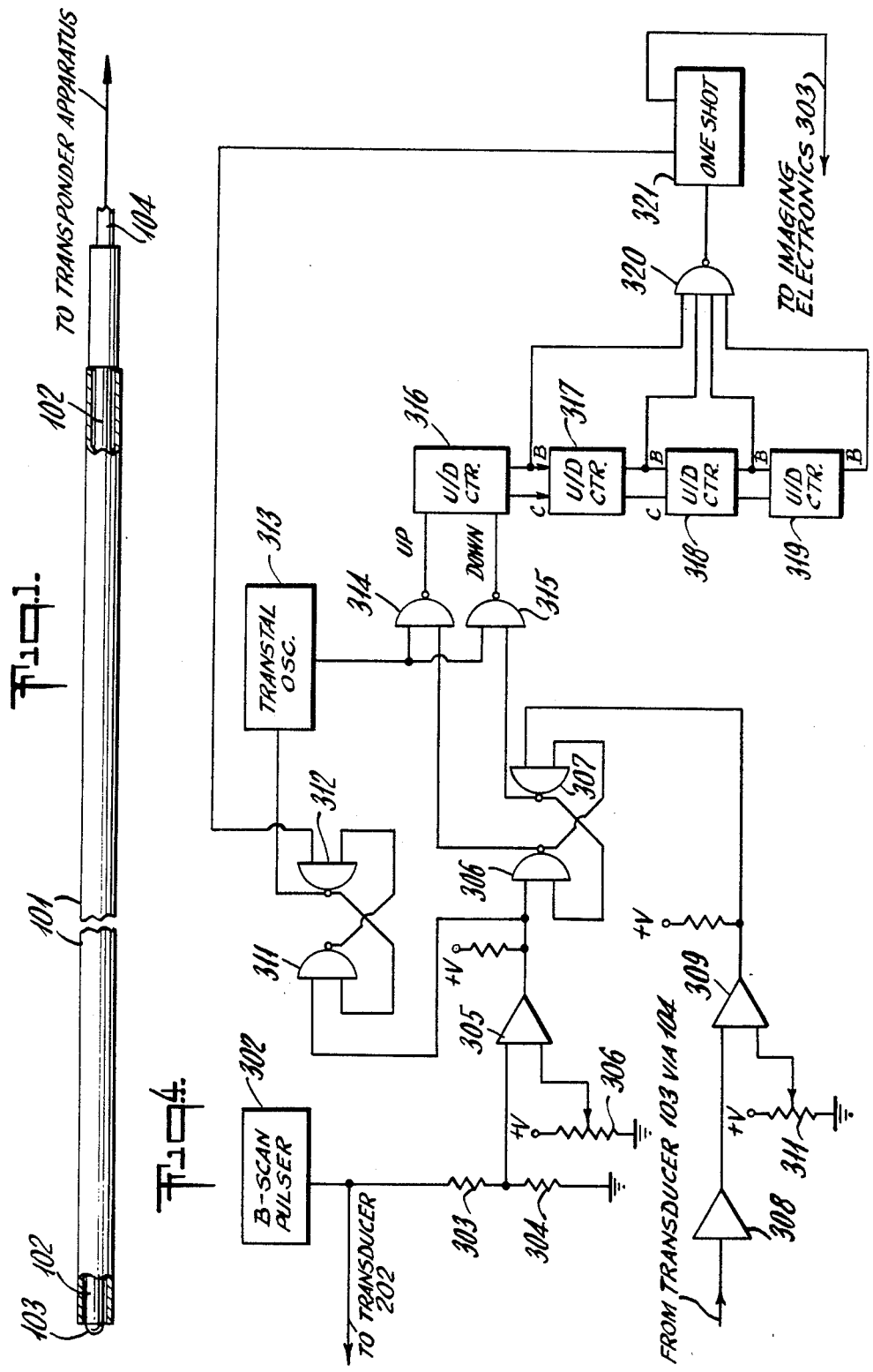

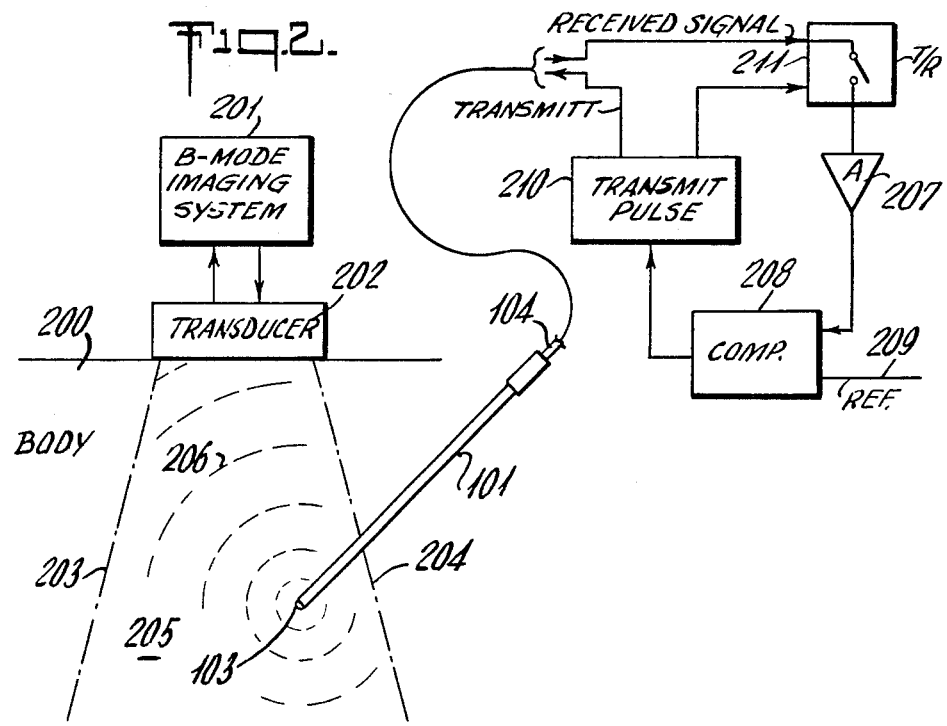
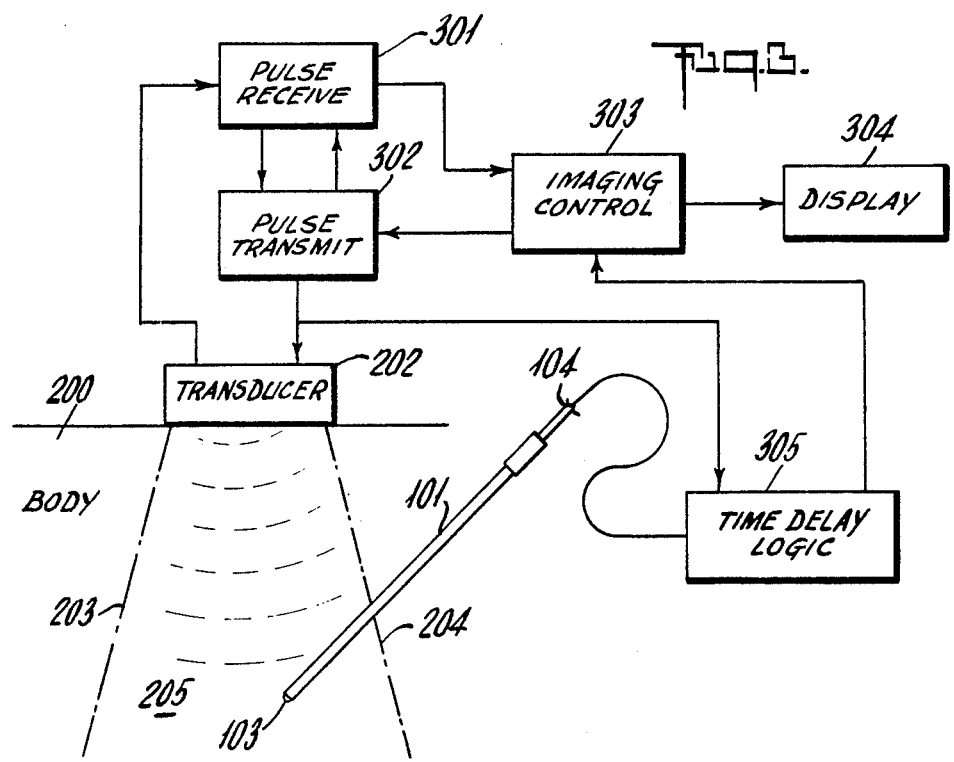

ULTRASOUND NEEDLE TIP LOCALIZATION SYSTEM

FIELD OF THE INVENTION

This invention relates to ultrasound imaging systems, and more particularly to the use of ultrasound tissue imaging systems for tissue aspiration sampling techniques.

BACKGROUND AND PRIOR ART

A conventional technique for obtaining tissue samples from deep within the body is aspiration biopsy. Aspiration biopsy is safe and minimally traumatic, utilizing a small, hollow needle which is inserted directly into the body, to a desired point, whereupon a tissue sample is withdrawn by vacuum aspiration. The aspiration needle is then withdrawn, and because of its relatively insignificant diameter, allows for wound closure by normal muscular and tissue tension, without the need for sutures, cauterization, or the like.

For effective aspiration biopsy, the tip of the needle must be accurately placed at the location of the tissues to be sampled, and it is a primary object of the present invention to provide means and methods for facilitating such placement.

A similar approach is utilized for location and removal of tissue lesions, such as in the breast. That is, with the aid of X-rays or the like, a needle is inserted into the breast until its tip is at the approximate location of the suspected lesion. The surgeon is thereby guided in order to perform a biopsy or other surgical procedure. This technique too suffers from dimensional/accuracy limitations associated with X-rays, and it is an object of the present invention to provide means and methods for facilitating such placement.

Ultrasound techniques have provided an excellent modality for in vivo imaging of relatively deep soft body tissue, offering conventional A-mode, B-mode, and C-mode approaches. Application of the A-mode to aspiration techniques is possible, wherein the needle is introduced down the center of the beam, through a hole in the transducer, and the needle tip is seen as a reflection due to the discontinuity of the ultrasound field at the needle tip. A-mode is not the preferred diagnostic approach, however, due to the relatively smaller information content of its output. Real time ultrasound imaging is available through a variety of B-mode and C-mode scanning techniques, such as moving, multiple, or phased array transducers, but these are relatively less suitable for aspiration techniques because the likelihood is great that an ultrasound pulse will have a non-perpendicular incidence to the aspiration needle point, and thereby not be reflected back to the transducer.

Hence, prior art approaches to ultrasound imaging of aspiration techniques are generally unsatisfactory, including A-mode aspiration transducers wherein the needle is introduced down the center of the beam by means of a hold in the transducer, and B-mode schemes wherein the needle is sought to be maintained perpendicular to the axis of propagation of the transducer.

It is an object of the present invention to provide ultrasound—aspiration systems and techniques whereby the former imaging modality and the latter biopsy technique are rendered mutually compatible, especially for real time B-mode or C-mode imaging systems, and including those which employ moving transducers.

It is a further object of the present invention to provide ultrasound systems and techniques whereby needle localization such as for breast lesions or the like is facilitated and rendered substantially more accurate.

SUMMARY OF THE INVENTION

In accordance with the principles of the present invention, a small, essentially point source omnidirectional ultrasound transducer is removably maintained substantially at the tip of an aspiration needle, and is coupled to external signal processing apparatus by means of electrical connections through the aspiration needle. As the needle is inserted into the body and into the field of an ultrasound imaging system, the imaging ultrasound pulses incident upon the needle transducer are acoustically/electrically sensed at the needle point transducer, whereby the location of the point may be incorporated into the imaging system based on the nature of the signal sensed at the needle point transducer. In one embodiment, the point source omnidirectional transducer at the needle point, upon sensing an incident pulse, is energized to transmit a signal of its own, which is sensed by the imaging system transducer and accordingly is directly incorporated into the assembled image. In an alternative embodiment, based on the timing of receipt of a signal at the needle point transducer, the delay of a return echo signal is electronically simulated, and thence superimposed onto the system image in the form of a composite.

DESCRIPTION OF THE DRAWINGS

FIG. 1 shows symbolically as aspiration needle system incorporating a transducer applicable to the principles of the present invention.

FIG. 2 shows a schematic diagram of a first illustrative embodiment of the present invention.

FIG. 3 shows a schematic version of a second illustrative embodiment of the principles of the present invention.

FIG. 4 shows a circuit schematic of a relevant portion of the apparatus included in the embodiment of FIG. 3.

BEST MODE FOR CARRYING OUT THE INVENTION

Referring first to FIG. 1, there is shown symbolically an aspiration needle system useful in accordance with the principles of the present invention. The FIG. 1 embodiment, shown in cross-section, includes a conventional aspiration needle 101 which is hollow in the center for vacuum aspiration of tissue samples once the needle is in place. This hollow axial channel formed by the needle 101 is useful in accordance with the principles of the present invention to carry a small, essentially point source omnidirectional transducer 103, carried at the end of an elongated support 102 which also carries appropriate conductors 104 from the transducer 103 to external transponder apparatus. Accordingly, the FIG. 1 embodiment may be inserted directly into human tissue as the needle 101 conventionally would be done, whereby the transducer 103 will, in accordance with the principles of the present invention, be utilized precisely to locate the position of the tip of the needle 101. Small, omnidirectional transducers which function essentially as point sources/receivers are commercially available, and typically are hemispherical in shape. It will be appreciated that the actual size of the transducer 103 and its support 102 will be determined by the dimensions of the needle 101, since upon appropriate positioning of the needle 101 with the point situated for aspiration of a sample of the correct tissue, the entire mechanism 102, 103, and 104 will be withdrawn from the needle. Hence, the support 102 for the transducer 103 functions not only as a physical and electrical connector to external apparatus, but also as a means for withdrawing the transducer 103.

FIG. 2 shows a preferred embodiment of the principles of the present invention wherein a needle 101 is inserted into a body 200. As shown, a B-mode imaging system 201 has a transducer 202 which is automatically coupled to the body 200, and which ultrasonically illuminates an imaging field 205 bounded by extremities 203 and 204. It will be understood that numerous such ultrasound imaging systems are commercially available, and the principles of the present invention are not limited to any particular one, or to any particular operational mode of the transducer 202, whether transducer motion, transducer signal phasing, combinations of these, or the like should be employed. Likewise, it is understood that signals to and from the transducer 202 may be acoustically coupled with the body 200 in any of a variety of well-known ways, including water paths, gel-type coupling media, and the like. As shown, the needle 101 has penetrated the body 200 and the point thereof, including transducer 103, is located within the field 205 of the tranducer 202. Under such circumstances, acoustic pulses from the transducer 202, when incident upon the point-source transducer 103, will result in an electrical signal at connecting cable 104, which is then amplified at 107 and compared at 208 with a suitable reference 209. Transmit/receive switch 211, normally closed, is opened by transmitter 210 prior to generation of a transmit pulse from 210. As is known in the art, race conditions and artifacts are thereby avoided. The reference 209 is selected as an appropriate noise/artifact rejection threshold, whereby the output of comparator 208 is enabled upon receipt of true imaging pulses from transducer 202, but otherwise is disabled. Upon detection of such a "true pulse" representation, comparator 208 energizes pulse transmission electronics 210, which in turn fires the omnidirectional point-source transducer 103 to emit a signal pulse (shown in phantom as 206), which is sensed by transducer 202 and incorporated in the image produced by system 201.

Schematic circuit elements 207, 208, and 210 are conventional items, and function without substantial delay (e.g. 1 microsecond) whereby transmission of a pulse from transducer 103 is, relative to the acoustic transmission in body 200, substantially instantaneous. Hence, the pulses from transducer 103 to systems transducer 202 will be "seen" by imaging transducer 202 and system 201 as a reflected echo from the location of point 103, for purposes of assembly of an image of the field 205.

On a real-time scale, then, the needle 103 may be manipulated externally while the user observes the image from system 201, whereby the point 103 is precisely located (e.g., 0.75 mm accuracy) for withdrawal of a sample. Thereupon, the omnidirectional transducer 103 is withdrawn from needle 101, thereby opening the channel within needle 101 for aspiration withdrawal of tissue, in conventional fashion. Subsequently, the needle 101 is withdrawn.

FIG. 3 shows an alternative embodiment of the principles of the present invention. The basic premise of the FIG. 3 embodiment is, rather than generating a return signal as done in the FIG. 1 embodiment, to simulate that return pulse by utilization of a simulated "time of flight" delay, and thereupon to produce a composite picture utilizing a superposition of the tissue image with a representation of the needle point.

In FIG. 3, transducer 202 illuminates an imaging field 205 bounded by lines 203 and 204 in the body 200. Again, the aspiration needle 101 is shown inserted with the point 103 being somewhere within the transducer field 205. In FIG. 3, the imaging system is shown symbolically divided into respective functional apparatus including pulse transmission electronics 302, pulse receipt electronics 301, imaging control apparatus 303, and a display 304. It will be appreciated that all such apparatus is conventional, and that substantially all ultrasound imaging systems can be functionally divided into these aspects.

In FIG. 3, the transducer 103 is connected via 104 to a time delay logic unit 305, which is shown also having connections to pulse transmit enable unit 302, and to the imaging control 303. Whenever a pulse transmission is enabled at transducer 202 by pulse transmit unit 302, the time delay logic 305 is conditioned. Upon receipt of the same pulse at point-source transducer 103, the time delay logic is enabled to calculate the "time of flight" of that pulse, or duration of transmission of the pulse from transducer 202 to transducer 103. Correspondingly, it is this same time which will be taken up for reflection of the pulse from the tissue at point 103 back to transducer 202, or would be required for transmission of a generated pulse from transducer 103 to imaging transducer 202. Based on this premise, the time delay logic 305 then delays incorporation of the representation of recept of the pulse at 103 by the calculated "time of flight," thereupon to convey that information to the imaging control 303, at the same time as an image is being assembled based on the reflected pulse wave fronts which first were issued from transducer 202, thence reflected from point 103 and from other areas in the field, to be detected by transducer 202 and pulse receiver circuitry 301. Accordingly, the imaging control 303 produces a superposition of two sets of signals, one being the total image field based on reflections back to transducer 202 (as in conventional ultrasound imaging), and the other being a representation of the location of the point transducer 103, based upon the delayed receipt of the incident signal from transducer 202. This composite image is coupled to the display 304 to be viewed, advantageously in real-time fashion. The appropriate superposition of disparate signals at the imaging control 303 may be accomplished advantageously utilizing commercially available digital scan converters, which are utilized in many commercial units for generation of a real-time display.

Referring to FIG. 4, there is shown a preferred embodiment for the time delay logic unit 305 of FIG. 3. The basic premise upon which the FIG. 4 circuitry is based is the initiation of accumulation of a count at the time of transmission of a pulse from transducer 202 and the termination and reversal of accumulation of that count upon receipt of the same pulse at point-source transducer 103, whereupon the composite image is assembled as the accumulated count goes back to zero.

The pulse transmit unit 302, shown in FIG. 4 as a B-scan pulser, couples a pulse enable signal to transducer 202, and simultaneously couples that signal, appropriately attenuated at resistance divider 303 and 304, to one input of a comparator amplifier 305. The other input of the comparator 305 is coupled to a reference level established at adjustable divider 306, such that the output of the comparator 305 becomes a logical "1" only upon issuance of a bona fide pulse from pulser 302. Noise and the like spurious signals are thereby prevented from having an erroneous effect on the logic of FIG. 4. Detection of a pulse by comparator 305 is coupled to set a pair of flip-flops 306–307 and 311–312, each being made up of cross-coupled Nand-gates. Flip-flop 311–312 then enables crystal oscillator 313 to commence generating output pulses at a known, predetermined rate, which pulses are coupled to Nand-gates 314 and 315.

The output logical "1" signal from comparator 305 also sets flip-flop 306–307, thereby delivering an enabling Nand-gate 314 and a disabling Nand-gate 315. Thereupon, each pulse cycle from crystal oscillator 313 provides a "count-up" pulse via gate 314 to a multistage up-down counter 316, 317, 318, and 319. Each such counter unit 316 through 319 is connected in conventional fashion with "carry" and "borrow" outputs, for sequential accumulation operation. Accordingly, the combined effect of comparator 305, flip-flops 306–307 and 311–312, oscillator 313, gate 314, and counters 316–319, is to commence accumulation of a count upon initiation of a pulse-energizing signal from pulser 302 to transducer 202.

Transducer 103 is coupled via amplifier 308 to another comparator 309, which has a noise rejection function by virtue of its comparison with the reference threshold from a variable divider 311. Hence, whenever an actual signal pulse is sensed by transducer 103, comparator 309 is enabled to reset flip-flop 306–307, in turn to disable gate 314 and to enable gate 315. Thereupon, pulses from the crystal oscillator 313 causes up-down counter unit 316–319 to count down, rather than up. Whenever the counters 316–319 thereby are all counted back to zero (i.e., the return "time of flight" corresponding to accumulation of the same amount of time between firing of a pulse at transducer 202 and receipt thereof at transducer 103), all "borrow" output terminals of counters 316–319 will be at a logical zero, and Nand-gate 320 will thereby be enabled to fire a one-shot 321. An output of the one-shot 321 is coupled to reset flip-flop 311–312, thereby disabling crystal oscillator 313. Further, an output of one-shot 321 is coupled to the imaging electronics 303, which thereupon processes a composite image including signals from the pulse receive circuitry 301 and the simulated echo from transducer 103. The composite image thereupon is seen at display 304.

In a preferred embodiment, the comparators 305 and 309 are those available from Fairchild, Inc. under the trade designation 760PC, the oscillator 313 is of the type available under the trade designation 740S124, and the counters 316–319 are of the type available under the trade designation 74193.

It will be evident to those of ordinary skill in the art that similar principles, and indeed identical signal processing and logic systems and circuits, may be utilized in the case of identification and locations of small lesions in deep soft tissue (e.g. the breast) for purposes of biopsy or surgical removal. The difference from aspiration systems, of course, is that the point source transducer located at the needle tip does not need to be removable from the needle point through a channel therein (although such would not be a deleterious design factor).

It will be appreciated that the foregoing presents preferred and illustrative embodiments of the principles of the present invention, but that numerous alternative embodiments will occur to those of ordinary skill in the art without departure from the spirit or the scope of the present invention.

We claim:

1. Apparatus for performing surgical procedures upon select, internal body tissues, comprising:
    (a) a pulse-echo ultrasound imaging system for imaging the area of the body including said tissues, said imaging system including first transducer means adapted to be acoustically coupled to the exterior of the body;
    (b) hollow needle means for insertion into the body in said area at an angle and in a direction which is independent of the angle and position of said first transducer means;
    (c) second omnidirectional, substantially point source transducer means, removably located at the tip of said needle means;
    (d) circuit means, electrically coupled to said second transducer means, for sensing receipt of an ultrasound pulse directly from said first transducer means; and
    (e) means, responsive to said first transducer means and to said circuit means, for producing a composite image of said area which incorporates the position of said second transducer means into an image assembled by said imaging system.

2. Apparatus as described in claim 1 and adapted for aspiration biopsy techniques, wherein said needle means is a hollow aspiration needle, and wherein said second transducer means includes means for withdrawing said transducer means from said needle.

3. Apparatus as described in claim 2 wherein said means for withdrawing comprises an elongated means carrying said omnidirectional point source ultrasound transducer at its tip, said elongated means being removably axially carried within said aspiration needle.

4. Apparatus as described in claim 1 wherein said means for incorporating comprises means, responsive to said circuit means, for energizing said second transducer means to generate an ultrasound signal pulse which is to be transmitted directly to, and in turn sensed by said first transducer.

5. Apparatus as described in claim 4 wherein said means for energizing comprises:
    (a) comparator means for eliminating spurious artifacts sensed by said circuit means from said second transducer means;
    (b) transmit enable means, responsive to said comparator means, for energizing said second transducer means to generate an ultrasound pulse.

6. Apparatus as described in claim 1 wherein said means for incorporating comprises:
    (a) means, responsive to said circuit means, for developing a representation of the direct transit time of a pulse from said first transducer to said second transducer; and
    (b) means, responsive to said means for developing a representation, for developing a composite image, assembly of said composite being time delayed, by said transit time, after a pulse from said first transducer is sensed by said circuit means, said composite image being based on echo signals received at said first transducer, and on pulse signals sensed at said second transducer.

7. Apparatus as described in claim 6 wherein said first named means for developing includes:
   (a) means for identifying the time of transmission of a pulse signal from said imaging transducer;
   (b) means for identifying the time of receipt of said pulse at said point source transducer; and
   (c) logic means for developing a representation of the elapsed time between said identified times, and for simulating an echo pulse based on said developed representation.

8. A method of monitoring and controlling tissue aspiration procedures comprising:
   (a) irradiating a body area utilizing pulse-echo ultrasound techniques employing a first, external transducer;
   (b) providing an omnidirectional ultrasound transducer means substantially at the tip of an aspiration needle;
   (c) inserting said needle into said body area at an angle and in a direction which is independent of the position and orientation of said external transducer; and
   (d) producing a composite image of said body area, including the point of said needle, based on pulse signals incident to said omnidirectional transducer directly from said first transducer, and upon ultrasound echo signals received by said first transducer.

9. A method as described in claim 8 wherein said producing step includes generating direct return signals from said omnidirectional transponder upon each said receipt of an incident signal.

10. A method as described in claim 8 wherein said producing step includes:
   (a) simulating a return echo from said omnidirectional transponder position to said first transponder, by delaying further response for a time equal to the time in flight of said incident pulse; and
   (b) thereupon producing a composite image.

* * * * *